(12) United States Patent
Chauveau et al.

(10) Patent No.: US 8,506,078 B2
(45) Date of Patent: Aug. 13, 2013

(54) METHOD FOR DETERMINING AT LEAST ONE GEOMETRIC POSTURAL PARAMETER WHEN FITTING A CORRECTIVE SPECTACLE FRAME ON THE FACE OF A WEARER IN THE ANATOMICAL POSTURE THEREOF

(75) Inventors: Jean-Pierre Chauveau, Charenton le Pont (FR); Konogan Baranton, Charenton le Pont (FR); Claude Pedrono, Charenton le Pont (FR)

(73) Assignee: Essilor International (Compagnie Generale d'Optique), Charenton le Pont (FR)

( * ) Notice: Subject to any disclaimer, the term of this patent is extended or adjusted under 35 U.S.C. 154(b) by 0 days.

(21) Appl. No.: 13/258,695

(22) PCT Filed: Apr. 15, 2010

(86) PCT No.: PCT/FR2010/000310
§ 371 (c)(1),
(2), (4) Date: Oct. 21, 2011

(87) PCT Pub. No.: WO2010/119190
PCT Pub. Date: Oct. 21, 2010

(65) Prior Publication Data
US 2012/0033178 A1 Feb. 9, 2012

(30) Foreign Application Priority Data
Apr. 17, 2009 (FR) ...................................... 09 01887

(51) Int. Cl.
*A61B 3/00* (2006.01)
*A61B 3/11* (2006.01)
*G02C 13/00* (2006.01)
(52) U.S. Cl.
CPC ................ *A61B 3/11* (2013.01); *G02C 13/005* (2013.01)
USPC .............. 351/200; 351/204; 351/246; 33/200

(58) Field of Classification Search
CPC ................................ A61B 3/11; G02C 13/005
USPC ................ 351/200, 204, 205, 206, 210, 246, 351/159.75, 159.76, 178; 33/200
See application file for complete search history.

(56) References Cited

U.S. PATENT DOCUMENTS 5,592,248 A * 1/1997 Norton et al. ................. 351/246
2009/0262302 A1 10/2009 Chauveau et al.
(Continued)

FOREIGN PATENT DOCUMENTS

FR 2 860 887 A1 4/2005
FR 2 906 047 A1 3/2008
(Continued)

OTHER PUBLICATIONS

International Search Report, dated Jun. 14, 2010, from corresponding PCT application.

*Primary Examiner* — Huy K Mai
(74) *Attorney, Agent, or Firm* — Young & Thompson (57) ABSTRACT

A method includes:
a) defining position-identification elements for identifying the position of a first frame of reference associated with a wearer's head in a second frame of reference associated with an image-capture device and for identifying the angle of inclination of the first frame of reference in the sagittal plane of the wearer's head about a center of rotation of the head;
b) capturing a series of at least two images of the wearer's head;
c) determining, in the second frame of reference, a position of the center of rotation;
d) identifying, in each image, the image of a first anatomical point of the wearer's face;
e) determining, in each image, the angle of inclination relative to a reference plane of an anatomical plane that is perpendicular to the sagittal plane and that contains the center of rotation and the first anatomical point;
f) comparing the angle with a predetermined value; and
g) determining the geometrical-and-postural parameter as a function of the comparison.

16 Claims, 3 Drawing Sheets

(56) References Cited

U.S. PATENT DOCUMENTS

2010/0128220 A1   5/2010   Chauveau
2010/0177186 A1   7/2010   Baranton
2010/0195045 A1   8/2010   Nauche et al.

FOREIGN PATENT DOCUMENTS

| | | |
|---|---|---|
| FR | 2 914 173 A1 | 10/2008 |
| FR | 2 915 290 A1 | 10/2008 |
| WO | 2009/024681 A2 | 2/2009 |

\* cited by examiner

METHOD FOR DETERMINING AT LEAST ONE GEOMETRIC POSTURAL PARAMETER WHEN FITTING A CORRECTIVE SPECTACLE FRAME ON THE FACE OF A WEARER IN THE ANATOMICAL POSTURE THEREOF

BACKGROUND OF THE INVENTION

1. Field of the Invention

The present invention relates to a method of determining at least one geometrical-and-postural parameter for placing a frame of vision-correcting eyeglasses on the face of a wearer in the anatomical posture.

2. Description of the Related Art

In the context of mounting vision-correcting ophthalmic lenses in an eyeglass frame, it is presently preferred to take best account of individual geometrical-and-postural parameters associated with the wearer and the frame selected by the wearer, which parameters are referred to as personalized optical design parameters.

The looked-for geometrical-and-postural parameters are associated both with the shapes of the wearer's head and of the selected eyeglass frame, and also with the wearer's posture. They comprise in particular the three-dimensional configuration of each lens relative to the wearer's head under wearing conditions. This three-dimensional configuration is determined in particular by the pantoscopic angle of each lens when worn (the angle formed between the general plane of the lens relative to the vertical) and the heights of the wearer's eyes relative to the bottom edges of the lenses.

In order to determine this three-dimensional configuration, the optician places a pair of presentation eyeglasses on the wearer's nose. The presentation eyeglasses comprise the frame selected by the wearer together with non-correcting lenses mounted in the rims of the frame.

The height of the wearer's eyes relative to the bottom edge of the frame can be measured manually: the optician faces the wearer from in front and uses a rule to estimate a measurement of the distance between the pupil of an eye and the bottom edge of the presentation lens.

Proposals have been made to automate determining these geometrical-and-postural parameters on the basis of one or more captured images of the wearer wearing the selected eyeglass frame. The images are processed in order to determine the looked-for parameters.

Nevertheless, those methods of determining the geometrical-and-postural parameters of the wearer, regardless of whether they are manual or automated, suffer from considerable inaccuracy. In order to be able to obtain an accurate measurement whether by using a rule or by processing captured images, it is necessary for the wearer's head to be in the anatomical posture when the measurement is made or the images are captured. This anatomical posture is also referred to as the orthostatic position.

Unfortunately, for reasons of speed of execution and of comfort for the optician and for the wearer, the position of the wearer's head while taking the image is not monitored. However, if the angle of inclination of the head in its sagittal plane departs from the anatomical posture by 1 degree, there will be an error of 1 degree in the measurement of the pantoscopic angle and an error of 0.5 millimeters in the measurement of the heights of the eyes.

BRIEF SUMMARY OF THE INVENTION

In order to remedy those drawbacks of the state of the art, the invention proposes a method of determining geometrical-and-postural parameters of the wearer that ensures for the optician that these parameters are determined in the wearer's anatomical posture.

For this purpose, the invention provides a method of determining at least one geometrical-and-postural parameter for positioning a frame of vision-correcting eyeglasses on the face of a wearer in the anatomical posture, wherein the following steps are performed:

a) defining position-identification means on the wearer's head and/or on the eyeglass frame worn by the wearer in order to identify:
  the position of a frame of reference associated with the wearer's head in a frame of reference associated with an image-capture device; and
  the angle of inclination of said frame of reference associated with the wearer's head in the sagittal plane of the wearer's head about a center of rotation of the wearer's head;

b) capturing a series of at least two images of the head of said wearer by means of the image-capture device;

c) determining, in the frame of reference associated with the image-capture device, at least one position of the center of rotation of the wearer's head in the sagittal plane;

d) in each of said at least two captured images, identifying the image of at least one first remarkable anatomical point of the wearer's face;

e) for each of said at least two captured images, determining the angle of inclination relative to a reference plane known in the frame of reference associated with the image-capture device of an anatomical plane of the wearer's head that is perpendicular to the sagittal plane and that contains said center of rotation and said at least one first anatomical point;

f) comparing said angle of inclination with a predetermined value; and g) determining the looked-for geometrical-and-postural parameter as a function of the result of said comparison.

The selected anatomical plane is a plane of known angle of inclination in the anatomical posture.

The normal anatomical posture of the wearer's head corresponds to the position of the wearer's head in three dimensions for which Frankfurt's plane of the wearer's head lies in a horizontal plane. It is also said that the wearer is then in an orthostatic position, a position in which least effort is required.

Frankfurt's plane is defined as being the plane containing the lower orbit points OR and the porion PO of the wearer, where the porion is the highest point in the skull of the acoustic meatus, corresponding to the tragion TR of the ear, i.e. the highest point of the tragus of the ear.

Thus, by selecting an anatomical plane of orientation relative to Frankfurt's plane that is close to a known value that is statistically determined for a given population of individuals, the orientation of said anatomical plane in the anatomical posture of the wearer can easily be determined.

By means of this method, it is determined which images in the series of images captured of the wearer's head are the closest to the wearer being in the anatomical posture so as to be able to determine the geometrical-and-postural parameters of the wearer directly from an image that is close to the anatomical posture, or so as to calculate them for the anatomical posture.

The accuracy with which the geometrical-and-postural parameters are determined in this way is increased, thereby enabling ophthalmic correcting lenses to be fitted more accurately to the selected frame and optimizing wearer comfort.

According to a first advantageous characteristic of the method of the invention, in step g):

the image in said series of captured images is selected for which the difference between the angle of inclination as determined in step e) and said predetermined value is the smallest; and the looked-for geometrical-and-postural parameter is determined by processing said selected image.

The parameters are thus determined quickly and easily without any step including additional calculations.

According to another advantageous characteristic of the method of the invention, in step g):

the calculated geometrical-and-postural parameter is corrected as a function of the difference between the angle of inclination as determined in step e) for the selected image and said predetermined value.

According to another advantageous characteristic of the method of the invention, in step g):

the two images of said series of captured images are selected so that the difference between the angle of inclination determined in step e) and said predetermined value is the smallest;

on the basis of said two selected images, a model is calculated of at least a portion of the wearer's face corresponding to the image that would have been captured if the value of the angle of inclination of said anatomical plane was equal to said predetermined value; and on the basis of said model, the looked-for geometrical-and-postural parameter is determined.

The geometrical-and-postural parameters are thus determined very accurately.

According to another advantageous characteristic of the method of the invention, in step a), said position-identification means comprise a position-identification device mounted directly on the wearer's head or on the frame of the wearer's eyeglasses. These position-identification means may also include contactless three-dimensional measurements of the wearer's head with the selected frame in position thereon.

By way of example, the position-identification device is in the form of an accessory that can easily be clipped onto the wearer's eyeglass frame or that can be fitted onto the wearer's head. Using an image of such a device, it is possible to fully determine its position and orientation relative to the image-capture device.

In a variant, said position-identification means comprise identifying marks placed on the wearer's head.

According to another advantageous characteristic of the method of the invention, in step d), on each of said at least two captured images, the image is identified of at least one nasal or temporal corner of an eye of the wearer, and in step e), the angle of inclination is determined of the anatomical plane of the wearer's head containing said corner and the center of rotation corresponding to said image.

According to another advantageous characteristic of the method of the invention, in step d), in each of said at least two captured images, the position of the lowest point of the wearer's nose, referred to as the sub-nasal point, is identified, and in step e), the angle of inclination is determined of the anatomical plane of the wearer's head containing said sub-nasal point and the center of rotation corresponding to said image.

According to another advantageous characteristic of the method of the invention, in step g), the geometrical-and-postural parameter that is determined comprises at least one of the following magnitudes:

the pantoscopic angle of the frame worn by the wearer; and the heights of the centers of rotation of the wearer's eyes relative to the bottom edge of the frame.

According to another advantageous characteristic of the method of the invention, in step b), the wearer performs a vertical nodding movement of the head substantially in the sagittal plane, and a series of at least two images of the wearer's head is captured by the image-capture device for at least two different angles of inclination of the head.

In which case, advantageously, in step c), the position of the center of rotation (Ai) is determined from the positions and the angles of inclination of the frame of reference associated with the wearer's head as provided by the position-identification means and corresponding to at least two of said captured images.

Furthermore, in step c), the position of the center of rotation is determined from the positions and the angles of inclination of the frame of reference associated with the wearer's head and corresponding to a group of images that were captured in succession in said series of images.

In a first variant of the method of the invention, in step b), all of the captured images of the wearer are substantially frontal images of the wearer, i.e. images captured in a plane that is substantially perpendicular to the sagittal plane of the wearer's head.

In a second variant of the method of the invention, in step b), at least one substantially profile image of the wearer's head is captured, i.e. an image is captured in a plane substantially parallel to the sagittal plane of the wearer's head; and in step c), the determination of the position of said center of rotation of the wearer's head comprises identifying a second remarkable anatomical point in said substantially profile image captured in step b).

In which case, advantageously, in step c), said second remarkable anatomical point is identified:

by processing said substantially profile image captured in step b) and by recognizing in said image a shape associated with said second remarkable anatomical point; or by displaying said substantially profile image captured in step b) on a screen and by using pointer means to point to said second remarkable anatomical point.

BRIEF DESCRIPTION OF THE DRAWINGS

The following description with reference to the accompanying drawings that are given by way of non-limiting example shows clearly what the invention consists in and how it can be reduced to practice.

In the accompanying drawings.

DETAILED DESCRIPTION OF THE PREFERRED EMBODIMENTS

In the following description, the optician determines the geometrical-and-postural parameters of the wearer wearing an eyeglass frame 10 in the wearing configuration, the wearer taking up the anatomical posture.

These parameters are then used for mounting ophthalmic lenses in the frame.

The wearer may be in a sitting or a standing configuration.

The facial plane, referred to as the eye vertical plane PVO, is the plane perpendicular to Frankfurt's plane containing the centers of rotation CROG and CROD of the eyes.

The sagittal plane PSAG, or vertical midplane of the wearer's head, is the plane orthogonal to the eye vertical plane PVO and to Frankfurt's plane PF, passing via the middles of the centers of rotation CROD and CROG of the eyes OD and OG.

The right-bisector AO of the eyes OD and OG corresponds to the line of intersection between the sagittal plane PSAG and Frankfurt's plane PF.

Camper's plane is the plane containing the two porions and the bottom point of the nose, referred to as the sub-nasal point.

The neuro-orbital plane PNO is the plane containing the two porions and the intercanthic points, i.e. the corners of the eyes situated on the nose side of each eye.

The looked-for geometrical-and-postural parameters are obtained herein from captured images of the wearer wearing the frame 10 of the selected eyeglasses. The frame 10 receives presentation lenses 100, 101 that are non-correcting and that for sales and measurement-taking purposes are fitted to the frame where they take the place of the correcting lenses that are to be provided, and where they serve to determine geometrical-and-postural parameters relating to the wearer and to the frame.

The pair of presentation eyeglasses comprises the frame 10 selected by the wearer and right and left presentation lenses 100 and 101 (that are not correcting lenses). In the example shown in FIG. 2, the pair of eyeglasses is of the rimmed type, i.e. the lenses are mounted in the rims 11 and 12 of the frame 10.

In a variant, the pair of presentation eyeglasses may be of the rimless type, i.e. the lenses are pierced and each of them is held by one end of the nasal bridge and by one end of the temple associated with the lens, with the bridge and the temples co-operating with drilled holes.

By way of example, the looked-for geometrical-and-postural parameters are the following:

the orientation of each correcting lens for mounting in the frame relative to the wearer's head, and in particular the pantoscopic angle AMV (FIG. 3) between the mean plane PMC of the two lenses 100, 101 (or indeed the two rims 11, 12 of the frame 10) and the eye vertical plane PVO; and the distance H (FIG. 2) in the wearing configuration between the bottom edge of the lens and the pupil or the center of rotation of the corresponding eye of the wearer in a vertical direction parallel to the sagittal plane PSAG, referred to as the eye height H.

Figure 2:
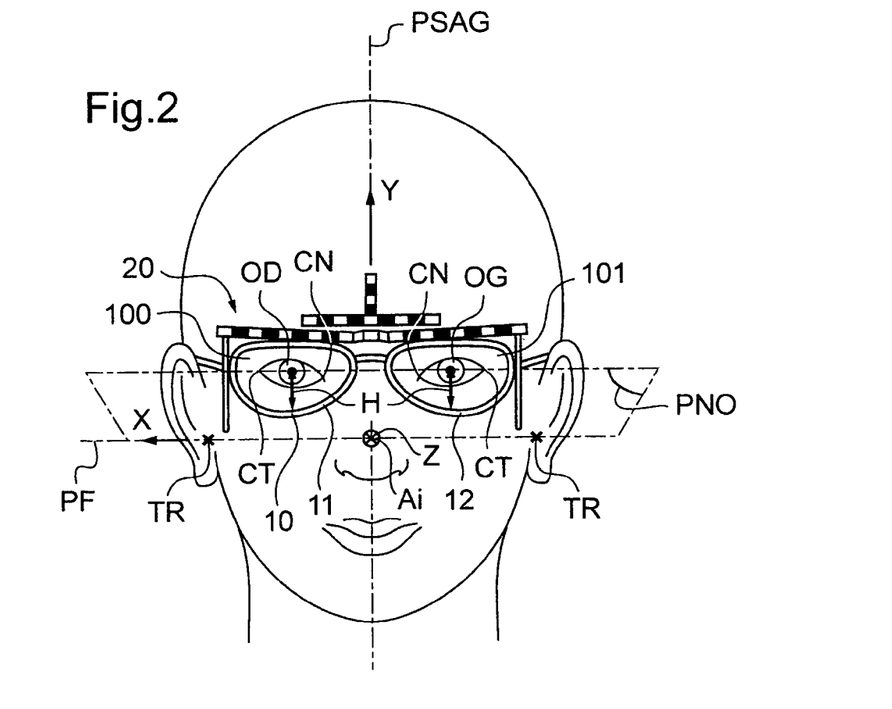
FIG. 2 is a face view of the head of a wearer in the anatomical posture and wearing presentation eyeglasses and a position-identification device.

This eye height H also corresponds to the distance between the inside face of the rim 11, 12 of the frame 10 and the pupil or the center of rotation of the corresponding eye OD, OG of the wearer in said direction for a rimmed eyeglass frame, as shown for example in FIG. 2.

Device

Figure 1:
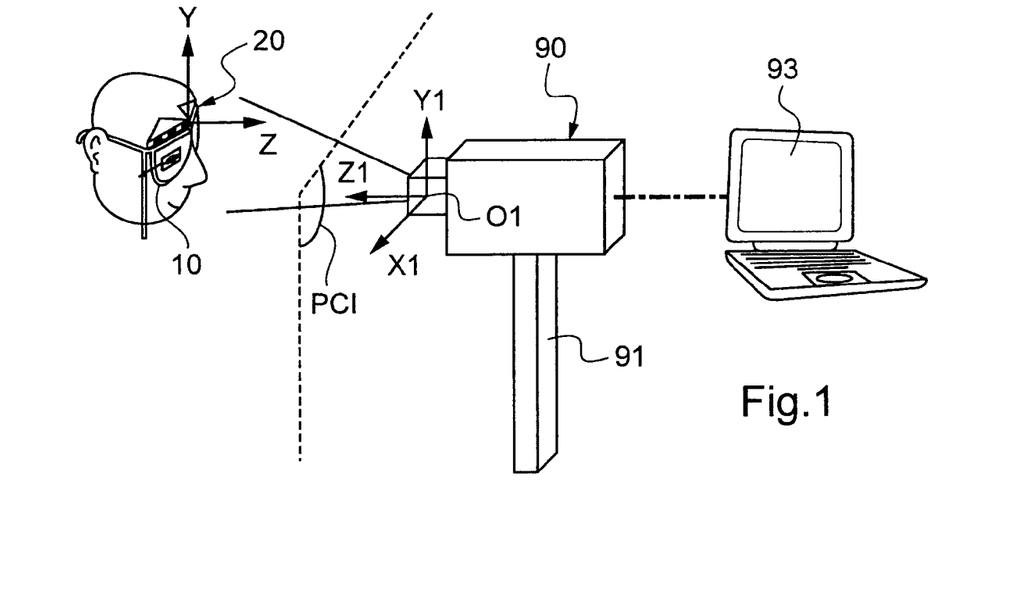
FIG. 1 is a perspective view of the FIG. 2 position-identification device fastened on the pair of presentation eyeglasses and of an image-capture device in communication with a processor and calculation system.
Figure 5:
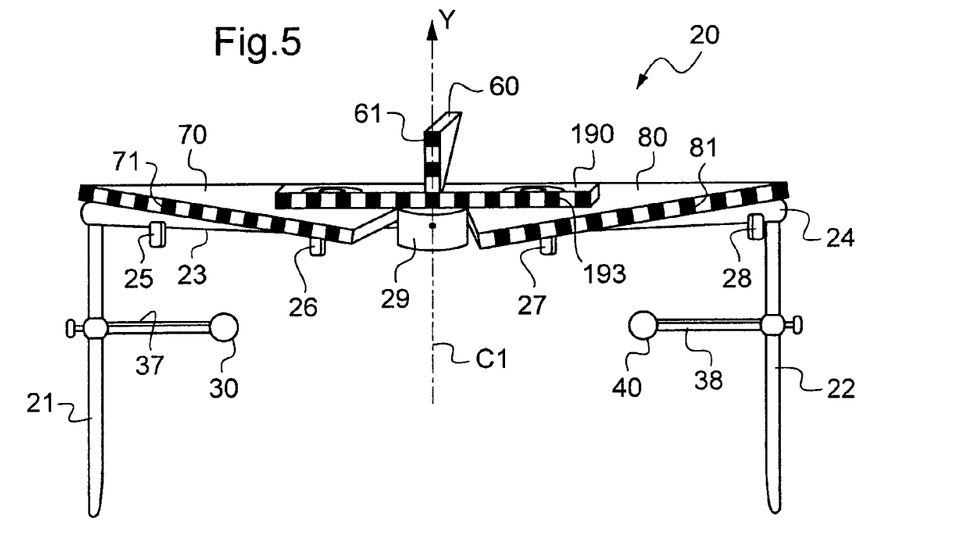
FIG. 5 is a face view of the position-identification device of FIG. 2.

In FIGS. 1 and 5, there can be seen a device for determining individual geometrical-and-postural parameters of a wearer wearing a pair of presentation eyeglasses.

The device includes an image-capture device 90 for capturing the image of a position-identifying device 20 mounted on the frame 10 in the wearing position, the image being captured in an image-capture plane PCI. The device also includes means for identifying position in a frame of reference associated with the image-capture device, and for identifying the angle of inclination of a frame of reference associated with the wearer's head, said angle of inclination being determined in the sagittal plane of the wearer's head.

The image-capture device 90 may be stationary or movable in the terrestrial frame of reference. When it is movable in the terrestrial frame of reference, the image-capture device 90 includes means for determining its position and its angle of inclination in the terrestrial frame of reference. These determination means may for example comprise an inclinometer and/or an accelerometer.

The image-capture device 90 is connected to a processor and calculation system 93 for acting on the captured image.

The image-capture plane PCI may be oriented in various ways relative to the wearer's head.

Figure 3:
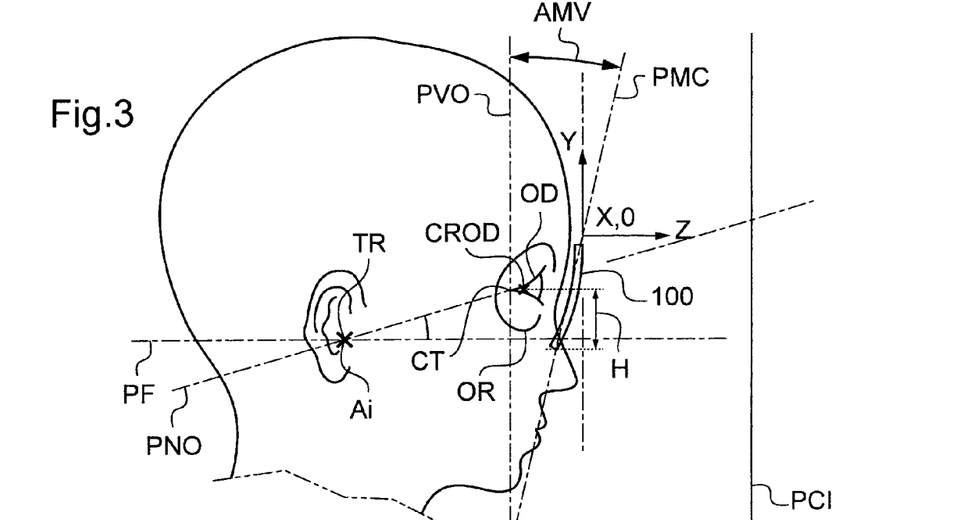
FIG. 3 is a profile view of the head of a wearer in the anatomical posture and wearing presentation eyeglasses and a position-identification device.

In the example shown in FIG. 3, the image-capture plane PCI is frontally oriented. This frontal image-capture plane PCI is defined as being perpendicular to the sagittal plane PSAG and to Frankfurt's plane PF of the wearer's head in the anatomical posture. It is the plane of FIG. 2.

In a variant, the image-capture plane of the image-capture device may extend in a plane parallel to the sagittal plane of the wearer's head, such that the captured image is then a profile image of the wearer's head.

The image-capture plane may also be oriented so as to capture a three-quarter image of the wearer's head.

Said position-identification means may include markers arranged on the wearer's head, constituted by remarkable points of the wearer's face, or by a device fitted on the wearer's head and having known shapes. The device may be constituted by the eyeglass frame itself or by a device fitted on the frame.

After a step of calibrating the position-identification means, the projection of these position-identification means into the image-capture plane, which modifies the apparent shape of said position-identification means, gives access to the position in a frame of reference associated with an image-capture device and to the angle of inclination of the frame of reference associated with the wearer's head, as determined in the sagittal plane of the wearer's head.

As shown in FIG. 3, the frame of reference associated with the frame and thus associated with the wearer's head is defined as an orthogonal axis system (O,X,Y,Z) and is embodied by the position-identification device 20. The center O of the axis system of this frame of reference is the middle of the segment interconnecting the fastener clamps 26 and 27. The X axis is horizontal and passes via the clamps 26 and 27. The Y axis is perpendicular to Frankfurt's plane and is thus vertical when the wearer's head is in the anatomical posture.

The plane OYZ corresponds to the sagittal plane PSAG of the wearer's head and to the plane of symmetry of the frame.

The axis OZ is parallel to the right bisector AO of the eyes. The plane OXZ is substantially parallel to Frankfurt's plane PF and is thus horizontal when the wearer's head is in the anatomical posture (FIG. 3).

Figure 4:
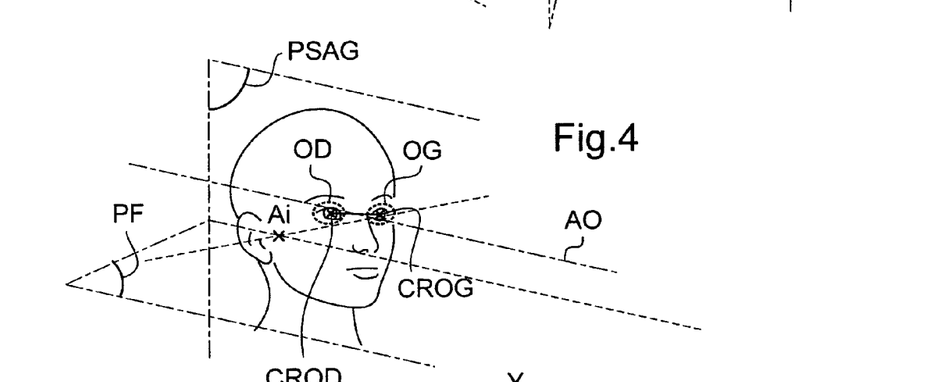
FIG. 4 is a perspective view of the head of a wearer in the anatomical posture.

The position-identification device 20 is shown in FIG. 4. This position-identification device 20 and the way in which it is used are described in detail in document FR 2 914 173. Only the main elements of the position-identification device 20 are recalled below.

The position-identification device 20 comprises a hinged linkage having two substantially rectilinear and substantially coplanar sticks 23 and 24 that are connected together by a hinge 29 having a hinge axis C1 that is substantially vertical in the wearing configuration.

Each stick 23,24 is provided with clamps 25, 26, 27, 28 that enable each stick 23, 24 to be fastened with freedom to pivot on the substantially horizontal top portion of the rim 11, 12 of the frame (FIGS. 2 and 4), or of the presentation lens when the eyeglasses are of the rimless type.

Each stick 23, 24 is surmounted by a horizontal position-identification element 70, 80 that is in the form of a triangular plate having a certain thickness with an edge face presenting a geometrical FIG. 71, 81 designed so that the geometrical configuration of said geometrical FIG. 71, 81 as projected into said image-capture plane PCI is representative of the horizontal component of the orientation of said horizontal position-identification element 70, 80 in the frame of reference associated with the wearer's head.

The horizontal component of the orientation of an element in the frame of reference associated with the wearer's head is defined by the angle between the longitudinal direction of said element and the plane OXY as projected into the plane OXZ. Likewise, the vertical component of the orientation of an element is defined by the angle between the longitudinal direction of said element and the plane OXY as projected into the plane OYZ.

The two horizontal position-identification elements 70, 80 are also connected together by a middle position-identification element 190 that is mechanically associated with the two horizontal position-identification elements 70, 80 in such a manner as to remain constantly in a fixed position relative to a vertical midplane of symmetry of said two elements 70 and 80, which plane coincides substantially with the plane of symmetry of the frame (that itself coincides substantially with the sagittal plane PSAG of the wearer's head).

This middle position-identification element 190 carries a geometrical FIG. 193 that is constituted in this example by dark strips that are spaced apart from one another by a known distance.

The image of these dark strips as seen in projection in the image-capture plane PCI by the image-capture device 90 makes it possible to calculate the distance between the position-identification device 20 and the image-capture device 90, and to determine the scale factor of the captured image.

The position-identification device 20 also includes a vertical position-identification element 60 that is also constituted by a triangular plate of given thickness extending in a plane that is substantially perpendicular to the midplane of the two horizontal position-identification elements 70 and 80 associated with the lenses 100 and 101. This vertical position-identification element 60 is fastened on the top face of the holder bar 190 in its center.

On one of its edge faces that is to face towards the image-capture device 90, it presents a geometrical FIG. 61 constituted by geometrical patterns that, as above, are constituted by dark strips separated from one another by a known distance and extending in the longitudinal direction of the corresponding edge face of the position-identification element 60.

As a result, each dark strip is arranged substantially horizontally in the wearing configuration and the longitudinal direction of the geometrical FIG. 61 is substantially vertical.

The height of the dark strips as projected into the image-capture plane PCI makes it possible to determine the pantoscopic angle AMV of the frame 10 when the wearer's head is in the anatomical posture.

The horizontal position-identification elements 70 and 80, and the middle and vertical position-identification elements 190 and 60 of the position-identification device 20 thus make it possible, in a frame of reference associated with the wearer's head, to identify the angle of inclination of the position-identification device 20 in the sagittal plane about a center of rotation of the wearer's head, and, in a frame of reference associated with the image-capture device 90, to identify the position of the position-identification device 20.

The image-capture device 90 typically consists in a video camera or a digital camera that is portable or mounted on a support or a stand.

The optical axis of the image-capture device 90 preferably extends in a horizontal plane. The position and the angle of inclination of the image-capture device 90 in the example described herein remain stationary while capturing a series of images. In practice, the movement of the image-capture device 90 between two successive image captures is negligible in this example.

The position of the image-capture device 90 is such that the wearer's face is included in its image acquisition field.

In a variant, the image-capture device may be inclined relative to the terrestrial horizon at an arbitrary angle that is known or measured by an inclinometer, for example. A calibration step is then needed.

The frame of reference associated with the image-capture device 90 is defined as having an orthogonal axis system (O1,X1,Y1,Z1) in which the axis O1Z1 is the optical axis of the image-capture device 90.

In this example, the processor and calculation system 93 for acting on the acquired image includes a microcomputer having software installed for processing the acquired image. In a variant, provision may be made for the processor and calculation system to be an independent system comprising firstly a display screen for communicating the results obtained, and secondly connection means enabling these results to be communicated to other appliances. Provision may also be made for an independent processor system optionally to be incorporated in the image-capture device 90.

Method

The above-described determination device serves to implement the following method for determining at least one geometrical-and-postural parameter for positioning a frame of vision-correction eyeglasses on the face of a wearer in the anatomical posture.

As shown in FIG. 2, in a first step a) of the method of the invention, the optician places the pair of presentation eyeglasses surmounted by the position-identification device 20 on the wearer's nose. The wearer is in a sitting or a standing configuration.

As explained above, the position-identification device 20 serves to determine the position of the frame of reference associated with the wearer's head in the frame of reference associated with the image-capture device 90.

It also gives access to the difference, between two image captures, in the angle of inclination in the sagittal plane of the frame of reference associated with the wearer's head as observed in the frame of reference associated with the image-capture device 90.

In a second step b) of the method, the optician asks the wearer to perform a vertical nodding movement of the head in its sagittal plane PSAG, while keeping the sagittal plane of the head vertical and in a substantially constant position laterally, i.e. in the direction perpendicular to the sagittal plane. In practice, while capturing a series of images, the overall lateral movement of the sagittal plane of the head is kept to within less than about 5 degrees of angle relative to the image-capture device 90.

In practice, the wearer looks at his or her own reflection in a mirror and nods the head through an amplitude of about 20 degrees.

During this movement, the image-capture device 90 captures a series of at least two images of the wearer's head, each image corresponding to a different angle of inclination of the head in its sagittal plane in the frame of reference associated with the image-capture device.

Preferably, the image-capture device 90 records a series of images of the wearer's head, each image corresponding to a different angle of inclination of the wearer's head in its sagittal plane, and including at least one image in each one-degree interval lying within the total amplitude of the nodding of the head.

In another step c) of the method, the processor and calculation system 93 processes the captured images to determine the position of the center of rotation Ai of the wearer's head in the frame of reference associated with the image-capture device (FIGS. 2 and 3).

This determination is performed from the positions and the angles of inclination of the frame of reference associated with the wearer's head as provided by the position-identification means and corresponding to the captured images.

In the preferred circumstance of a series comprising a large number of captured images, in step c) the center of rotation is determined from the positions and the angles of inclination of the frame of reference associated with the wearer's head corresponding to images in said series that constitute a group of images that were captured in succession.

The processor and calculation system 93 preferably selects successive pairs of images from the series of captured images and determines the positions and the angles of inclination of the frame of reference associated with the wearer's head in the frame of reference associated with the image-capture device, which positions and angles are provided by the position-identification device 20, and the processor and calculation system 93 deduces therefrom the position of the horizontal center of rotation Ai of the wearer's head that is common to each selected pair of captured images.

Figure 6:
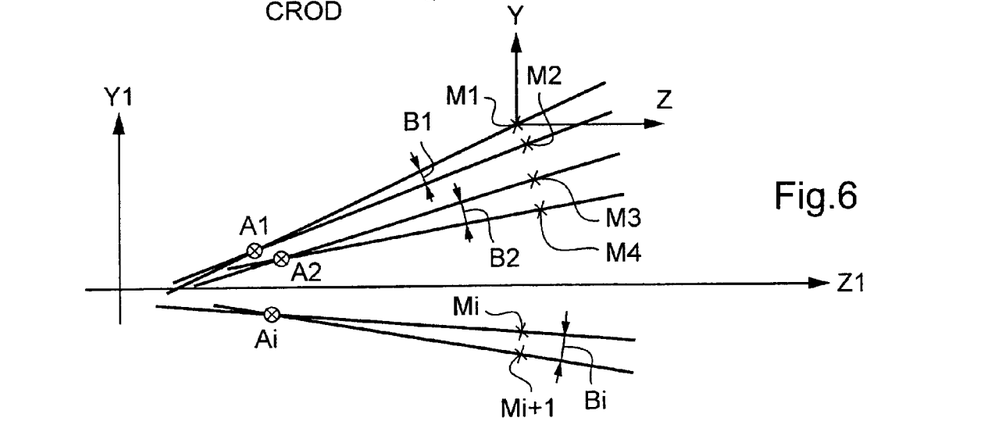
FIG. 6 is a diagrammatic view relating to the step of determining the instantaneous horizontal axis of rotation of the wearer's head.

This step is shown diagrammatically in FIG. 6.

While the wearer's head is nodding, the center of rotation Ai of the wearer's head moves in the sagittal plane. This movement is assumed to be negligible between two images that are captured in succession by the image-capture device. The movement of the center of rotation in the sagittal plane is assumed to be less than 5 millimeters.

The processor and calculation system 93 thus preferably calculates a plurality of positions for the center of rotation Ai corresponding to different groups of images captured in succession in said series of images, e.g. corresponding to each selected pair of successive images.

The processor and calculation system 93 processes each pair of successive images so as to determine the position of a particular point Mi of the frame of reference associated with the wearer's head in the image-capture frame of reference and so as to determine the difference Bi in the image-capture frame of reference of the angle of inclination of the frame of reference associated with the wearer's head between the two successive images that are being taken into consideration.

Specifically, the difference Bi in the image-capture frame of reference of the angle of inclination of the frame of reference associated with the wearer's head between two successive images is calculated from information provided by the position-identification device 20, by taking the difference between the angles of inclination of the position-identification device 20 in the frame of reference of the wearer's head as provided by said position-identification device 20 in the two images under consideration.

On the basis of the positions of the points Mi and of the difference Bi in the angle of inclination as calculated for two successive images, the processor and calculation system 93 deduces the position of the center of rotation Ai that corresponds to the pair of successive images under consideration. For each pair of images, this center of rotation Ai lies at the apex of an isosceles triangle whose angle at the apex is equal to the calculated difference Bi in the angle of inclination, as shown in FIG. 6.

In a step d) of the method, the processor and calculation system 93 identifies in each captured image the image ICNi of a first remarkable anatomical point CNi of the wearer's face.

Then, in a step e), for each captured image it determines the angle of inclination of an anatomical plane of the wearer's head, relative to a reference plane associated with the image-capture device, which anatomical plane contains said center of rotation Ai and said point CNi.

To do this, the processor and calculation system 93 acts for each pair of successive images in said series of captured images to determine the position of said point CNi of the wearer's face in the frame of reference associated with the image-capture device.

Figure 7:
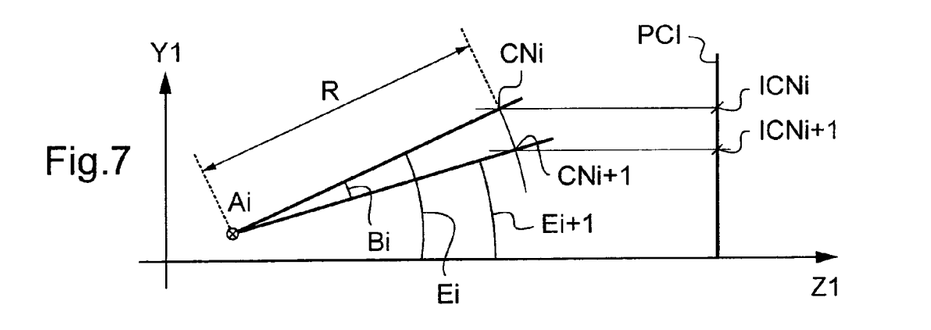
FIG. 7 is a diagrammatic view relating to the step of determining the angle of inclination of an anatomical plane relative to the reference plane associated with the image-capture device.

This step is shown diagrammatically in FIG. 7.

This figure shows two successive images of the series of captured images in superposition in the image-capture plane PCI, by indicating the position of the image ICNi of the first remarkable anatomical point CNi as identified in each of these images.

Since the image-capture plane PCI in this example is a frontal plane, the positions of the corresponding first remarkable anatomical points CNi of the wearer's face lie on a horizontal line passing via the identified images ICNi of these points CNi and perpendicular to the image-capture plane PCI.

In addition, these two points CNi are at equal distances from the center of rotation Ai as calculated in step c) and corresponding to the pair of images under consideration.

The difference Bi in angle of inclination in the sagittal plane about the center of rotation Ai of these points CNi is also known.

The processor and calculation system 93 solves the corresponding system of equations to deduce therefrom the position of the first remarkable anatomical point CNi of the wearer's face in the frame of reference associated with the image-capture device while the wearer's head is in the position corresponding to each captured image.

From the position of this first remarkable anatomical point CNi and the position of the corresponding center of rotation Ai, the processor and calculation system 93 determines the angle of inclination Ei of an anatomical plane of the wearer's head, relative to a reference plane associated with the image-capture device, which anatomical plane contains said center of rotation Ai and said remarkable point CNi. In this example the reference plane is a horizontal plane, and the anatomical plane is perpendicular to the sagittal plane of the wearer's head.

It is also possible at this point to envisage that the first remarkable anatomical point under consideration corresponds to the projection of a point of the wearer's face onto the sagittal plane, and that the processor and calculation system 93 calculates the angle of the line passing through said projected point and the center of rotation relative to the reference plane.

In a variant, the processor and calculation system 93 determines the positions of two first remarkable anatomical points and determines the angle of inclination of the anatomical plane of the wearer's head containing said center of rotation and said two first remarkable anatomical points relative to a plane of reference associated with the image-capture device.

In a step f) of said method, the processor and calculation system 93 compares this angle of inclination with a predetermined value.

In a first implementation of the method of the invention, in step d), the processor and calculation system 93 identifies the image of at least one nasal or temporal corner CN or CT of an eye OD, OG of the wearer in each captured image (see FIG. 2). In this example it preferably identifies the nasal corner CN of an eye of the wearer.

The nasal corners, known as intercanthic points, and the temporal corners, known as extracanthic points, of each eye are defined as being the extreme points of each eye situated beside the wearer's nose or temple.

In step e), the processor and calculation system 93 then determines the angle of inclination Ei of the anatomical plane of the wearer's head that is perpendicular to the sagittal plane and that contains said corner CN, CT and the center of rotation Ai corresponding to each image. This anatomical plane is called the neuro-orbital plane (PNO) and its angle of inclination relative to Frankfurt's plane is a morphological constant having a median value for a given population of individuals that is known statistically. The median value of this angle of inclination is equal to 7 degrees: this neuro-orbital plane is situated at about 7 degrees below Frankfurt's plane PF.

Thus, under such circumstances, the angle of inclination Ei of said anatomical plane containing the corner of the wearer's eye and the center of rotation of the wearer's head is compared with a predetermined value that lies in the range 5 degrees to 9 degrees, and that is preferably equal to 7 degrees.

It is also possible to envisage that said predetermined value is adjusted as a function of the wearer, in particular as a function of the wearer's age or ethnicity.

It is also possible to envisage identifying the images of two, three, or four nasal and/or temporal corners CN and/or CT of the eyes OD, OG of the wearer, and determining the angle of inclination of the mean anatomical plane containing these two, three, or four points.

In a second implementation of the method of the invention, in step d), the processor and calculation system 93 identifies the position of the bottom point of the wearer's nose in each captured image, and in step e) it determines the angle of inclination of the anatomical plane of the wearer's head containing said bottom point of the nose and the center of rotation corresponding to each image. This anatomical plane is called Camper's plane and its angle of inclination relative to Frankfurt's plane is a morphological constant having a median value for a given population of individuals that is known statistically. This median value of the angle of inclination is equal to −18 degrees: Camper's plane is situated about 18 degrees below Frankfurt's plane PF.

Under such circumstances, the angle of inclination of said anatomical plane containing the bottom point of the nose and the center of rotation of the wearer's head is then compared with a predetermined value that lies in the range −15 degrees to −21 degrees, and that is preferably equal to −18 degrees.

Finally, in a step g) of the method, regardless of which anatomical plane has its angle of inclination determined in step e), the processor and calculation system 93 determines the looked-for geometrical-and-postural parameter as a function of the result of the comparison.

To do this, in a first variant, in step g):
the processor and calculation system 93 selects the image in said series of captured images for which the difference between the angle of inclination Ei determined in step e) and said predetermined value is the smallest; and
the processor and calculation system 93 determines the looked-for geometrical-and-postural parameter by processing said selected image.

Such processing is described in detail in document FR 2 914 173.

Figure 8:
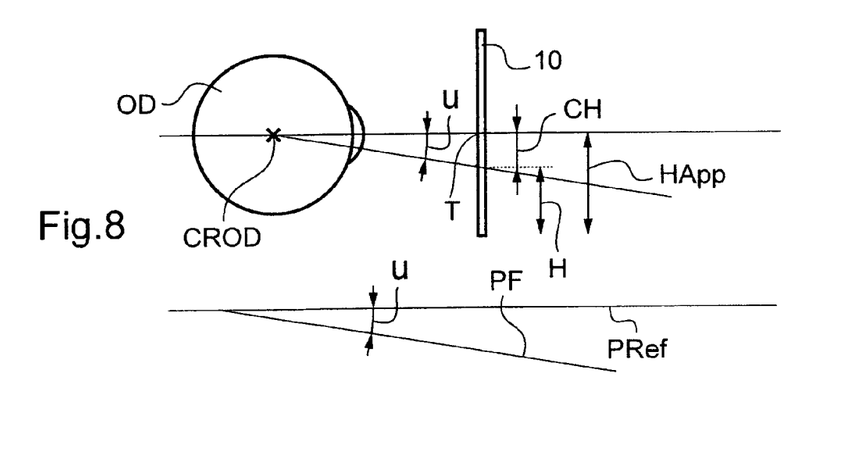
FIG. 8 is a diagrammatic view of a wearer's eye and the frame seen in a plane parallel to the sagittal plane and containing the eye in question, the view showing a step of correcting a determined geometrical-and-postural parameter.

Optionally, provision may be made for the processor and calculation system 93 to correct the calculated geometrical-and-postural parameter as a function of the difference U between the angle of inclination Ei determined in step e) and said predetermined value. This correction step is shown diagrammatically in FIG. 8. In FIG. 8, Frankfurt's plane PF of the wearer's head is inclined at an angle U relative to the horizontal reference plane PRef.

The apparent height HApp of the right eye OD, shown in FIG. 8, as determined by processing the corresponding image is equal to the height of said eye H as looked for in the anatomical posture of the wearer, i.e. when Frankfurt's plane PF is parallel to the horizontal reference plane PRef, plus an added error CH.

This error CH is equal to the distance between the center of rotation CROD of the eye and the frame, which distance is represented by the distance between the center of rotation CROD and its horizontal projection onto the mean plane of the frame 10 corresponding to the point T in FIG. 8 multiplied by the tangent of the angle of inclination U of Frankfurt's plane relative to the reference plane.

Provision may also be made for the processor and calculation system 93 to compare the value of the angle of inclination Ei as calculated in step e) as performed on the selected image with high and low threshold values that are equal to the predetermined value respectively plus or minus 0.5 degrees. If the angle of inclination Ei between the anatomical plane and Frankfurt's plane in the selected image is greater than the high threshold value or less than the low threshold value, then the processor and calculation system 93 informs the optician that it is necessary to capture another series of images.

In a second variant, in step g):
the processor and calculation system 93 selects the two images in said series of captured images for which the difference between the angle of inclination Ei as determined in step e) and said predetermined value is the smallest; and
on the basis of these two selected images, the processor and calculation system 93 calculates a model of at least a portion of the wearer's face corresponding to the image that would have been captured if the value of the angle of inclination Ei of said anatomical plane was indeed equal to said predetermined value.

By way of example, this model is determined by interpolating from the two selected images.

Thereafter the processor and calculation system 93 determines the looked-for geometrical-and-postural parameter by processing the calculated model of the wearer's face.

In a variant of the above, the position of the center of rotation of the wearer's head may be determined from an image that is substantially a profile view of the wearer's head.

Under such circumstances, in step b), there are captured at least one substantially profile image of the wearer's head, i.e. an image captured in a plane substantially parallel to the sagittal plane of the wearer's head, and at least one front image of the wearer's head, and preferably a series of at least two images of the wearer's head.

In step c), the determination of the position of said center of rotation of the wearer's then includes identifying a second remarkable anatomical point in said substantially profile image captured in step b) which second remarkable anatomical point corresponds to the tragion of the wearer's ear.

This second remarkable anatomical point may be identified as follows:
either by processing said substantially profile image captured in step b) and recognizing in said image a shape that is associated with said second remarkable anatomical point;
or else by displaying on a screen said substantially profile image captured in step b) and making use of pointing means to identify said second remarkable anatomical point.

The processor and calculation system then determines the position of the identified tragion in the frame of reference associated with the image-capture device and deduces therefrom the position of the center of rotation of the wearer's head in the sagittal plane in the frame of reference associated with the image-capture device. The center of rotation corresponds to the projection of said tragion of the wearer's head onto the sagittal plane.

The other steps of the method take place as described above.

Whatever the variant of the method that is used, the looked-for geometrical-and-postural parameter is thus determined either from an image of the wearer while very close to the anatomical posture, or from a model of the wearer in the anatomical posture. The accuracy with which the geometrical-and-postural parameter is thus determined is increased and the accuracy of the personalized design of the lenses is improved, thereby improving wearer comfort.

The present invention is naturally not limited to the implementations described and shown, and the person skilled in the art knows how to apply any variant in accordance with its spirit.

In particular, it is possible to envisage any type of position-identification means, in particular positioning marks placed on the wearer's head, e.g. marks drawn with a felt tip pen or stickers placed on the wearer's head.

The invention claimed is:

1. A method of determining at least one geometrical-and-postural parameter (H, AMV) for positioning a frame (10) of vision-correcting eyeglasses on a face of a wearer in an anatomical posture, wherein the following steps are performed:
a) defining position-identification means (20) on a wearer's head and/or on the eyeglass frame (10) worn by the wearer in order to identify:
a position of a frame of reference (O,X,Y,Z) associated with the wearer's head in a frame of reference (O1, X1,Y1,Z1) associated with an image-capture device (90); and
an angle of inclination of said frame of reference associated with the wearer's head in a sagittal plane (PSAG) of the wearer's head about a center of rotation (Ai) of the wearer's head;
b) capturing a series of at least two images of the head of said wearer by means of the image-capture device (90);
c) determining in the frame of reference associated with the image-capture device (90), at least one position of the center of rotation (Ai) of the wearer's head in the sagittal plane (PSAG);
d) in each of said at least two captured images, identifying an image of at least one first remarkable anatomical point (CNi) of the wearer's face;
e) for each of said at least two captured images, determining the angle of inclination (Ei) relative to a reference plane (PRef) known in the frame of reference (O1,X1, Y1,Z1) associated with the image-capture device (90) of an anatomical plane (PNO) of the wearer's head that is perpendicular to the sagittal plane (PSAG) and that contains said center of rotation (Ai) and said at least one first anatomical point (CNi);
f) comparing said angle of inclination (Ei) with a predetermined value; and
g) determining a looked-for geometrical-and-postural parameter (H, AMV) as a function of the result of said comparison.

2. The method according to claim 1, wherein, in step g):
the image in said series of captured images is selected for which the difference between the angle of inclination (Ei) as determined in step e) and said predetermined value is smallest; and
the looked-for geometrical-and-postural parameter (H, AMV) is determined by processing said selected image.

3. The method according to claim 2, wherein, in step g):
the calculated geometrical-and-postural parameter (H, AMV) is corrected as a function of the difference between the angle of inclination (Ei) as determined in step e) for the selected image and said predetermined value.

4. The method according to claim 1, wherein, in step g):
the two images of said series of captured images are selected so that the difference between the angle of inclination (Ei) determined in step e) and said predetermined value is smallest;
on a basis of said two selected images, a model is calculated of at least a portion of the wearer's face corresponding to the image that would have been captured if the value of the angle of inclination (Ei) of said anatomical plane (PNO) was equal to said predetermined value; and
on a basis of said model, the looked-for geometrical-and-postural parameter (H, AMV) is determined.

5. The method according to claim 1, wherein, in step a), said position-identification means (20) comprise a position-identification device (20) mounted directly on the wearer's head or on the frame (10) of the wearer's eyeglasses.

6. The method according to claim 1, wherein, in step a), said position-identification means comprise identifying marks placed on the wearer's head.

7. The method according to claim 1, wherein, in step d), on each of said at least two captured images, the image is identified of at least one nasal or temporal corner (CN, CT) of an eye (OD, OG) of the wearer, and in step e), the angle of inclination (Ei) is determined of the anatomical plane (PNO) of the wearer's head containing said corner (CN, CT) and the center of rotation corresponding to said image.

8. The method according to claim 1, wherein, in step d), in each of said at least two captured images, the position of the lowest point of the wearer's nose, referred to as the sub-nasal point, is identified, and in step e), the angle of inclination is determined of the anatomical plane of the wearer's head containing said sub-nasal point and the center of rotation corresponding to said image.

9. The method according to claim 1, wherein, in step g), the geometrical-and-postural parameter (H, AMV) that is determined comprises at least one of the following magnitudes:
  a pantoscopic angle (AMV) of the frame (10) worn by the wearer; and
  heights (H) of the centers of rotation (CROG, CROD) of the wearer's eyes relative to a bottom edge of the frame (10).

10. The method according to claim 1, wherein, in step b), the wearer performs a vertical nodding movement of the head substantially in the sagittal plane, and a series of at least two images of the wearer's head is captured by the image-capture device (90) for at least two different angles of inclination of the head.

11. The method according to claim 10, wherein, in step c), the position of the center of rotation (Ai) is determined from the positions and the angles of inclination of the frame of reference associated with the wearer's head as provided by the position-identification means (20) and corresponding to at least two of said captured images.

12. The method according to claim 11, wherein, in step c), the position of the center of rotation (Ai) is determined from the positions and the angles of inclination of the frame of reference associated with the wearer's head and corresponding to a group of images that were captured in succession in said series of images.

13. The method according to claim 12, wherein, in step c), a plurality of positions are determined for the center of rotation (Ai) corresponding to different groups of successively-captured images in said series of images.

14. The method according to claim 10, wherein, in step b), all of the captured images of the wearer are substantially frontal images of the wearer, i.e. images captured in a plane that is substantially perpendicular to the sagittal plane (PSAG) of the wearer's head.

15. The method according to claim 1, wherein:
  in step b), at least one substantially profile image of the wearer's head is captured, i.e. an image is captured in a plane substantially parallel to the sagittal plane (PSAG) of the wearer's head; and
  in step c), the determination of the position of said center of rotation (Ai) of the wearer's head comprises identifying a second remarkable anatomical point (TR), in said substantially profile image captured in step b).

16. The method according to claim 15, wherein, in step c), said second remarkable anatomical point (TR) is identified:
  by processing said substantially profile image captured in step b) and by recognizing in said image a shape associated with said second remarkable anatomical point (TR); or
  by displaying said substantially profile image captured in step b) on a screen and by using pointer means to point to said second remarkable anatomical point (TR).

* * * * *

UNITED STATES PATENT AND TRADEMARK OFFICE
CERTIFICATE OF CORRECTION

PATENT NO.       : 8,506,078 B2                              Page 1 of 1
APPLICATION NO.  : 13/258695
DATED            : August 13, 2013
INVENTOR(S)      : Chauveau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this

Fifteenth Day of September, 2015

Michelle K. Lee
*Director of the United States Patent and Trademark Office*